(12) United States Patent
Sakashita

(10) Patent No.: US 10,702,655 B2
(45) Date of Patent: Jul. 7, 2020

(54) METHOD FOR PRODUCING SYRINGE GASKET, AND SYRINGE INCLUDING THE GASKET

(71) Applicant: SUMITOMO RUBBER INDUSTRIES, LTD., Kobe-shi, Hyogo (JP)

(72) Inventor: Yuki Sakashita, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 155 days.

(21) Appl. No.: 15/970,500

(22) Filed: May 3, 2018

(65) Prior Publication Data

US 2018/0344939 A1    Dec. 6, 2018

(30) Foreign Application Priority Data

Jun. 2, 2017   (JP) ................. 2017-110359

(51) Int. Cl.
| | |
|---|---|
| *A61M 5/315* | (2006.01) |
| *A61M 5/31* | (2006.01) |
| *B23K 26/00* | (2014.01) |
| *B23K 103/00* | (2006.01) |
| *B23K 103/16* | (2006.01) |

(52) U.S. Cl.
CPC . *A61M 5/31513* (2013.01); *A61M 2005/3101* (2013.01); *A61M 2005/3131* (2013.01); *A61M 2207/00* (2013.01); *A61M 2207/10* (2013.01); *B23K 26/0006* (2013.01); *B23K 2103/172* (2018.08); *B23K 2103/42* (2018.08)

(58) Field of Classification Search
CPC ...... A61F 2/2418; A61F 2/013; A61F 2/2436; A61F 2/2409; A61F 2/2433; A61M 25/104; A61B 18/1492
See application file for complete search history.

(56) References Cited

U.S. PATENT DOCUMENTS

| | | | | |
|---|---|---|---|---|
| 3,628,523 A | * | 12/1971 | Pirtle, Jr. .............. | A61M 5/178 600/432 |
| 4,997,423 A | | 3/1991 | Okuda et al. | |
| 6,090,081 A | * | 7/2000 | Sudo ................. | A61M 5/31513 604/218 |
| 2004/0099994 A1 | | 5/2004 | Brinkhues | |

(Continued)

FOREIGN PATENT DOCUMENTS

| | | |
|---|---|---|
| JP | 63-97173 A | 4/1988 |
| JP | 10-314305 A | 12/1998 |

(Continued)

*Primary Examiner* — Manuel A Mendez
(74) *Attorney, Agent, or Firm* — Birch, Stewart, Kolasch & Birch, LLP

(57) ABSTRACT

The present invention provides a method for producing a syringe gasket which is improved in liquid drug sealability by forming a minute projection on a circumferential surface of the gasket after demolding the gasket. In a method for producing a syringe gasket including a cylindrical main body (2) made of an elastic material and an inert resin film (3) laminated on a surface of the main body (2), at least one minute projection (5) is formed as extending circumferentially of the gasket on a surface of the inert resin film (3) laminated on the main body (2) by thermal processing using a laser beam.

11 Claims, 1 Drawing Sheet

(56) References Cited

U.S. PATENT DOCUMENTS

| | | | | |
|---|---|---|---|---|
| 2006/0178643 A1* | 8/2006 | Sudo | .................. | A61M 5/31511 604/230 |
| 2009/0162530 A1* | 6/2009 | Nesbitt | ................ | A61L 29/106 427/2.3 |
| 2010/0012703 A1* | 1/2010 | Calabrese | ............ | A61B 17/068 227/176.1 |
| 2013/0040156 A1 | 2/2013 | Nakano et al. | | |
| 2013/0316110 A1 | 11/2013 | Sudo | | |
| 2016/0287800 A1 | 10/2016 | Nakano et al. | | |

FOREIGN PATENT DOCUMENTS

| | | |
|---|---|---|
| JP | 2004-525011 A | 8/2004 |
| JP | 2006-181027 A | 7/2006 |
| JP | 4908617 B2 | 4/2012 |
| JP | 2013-244668 A | 12/2013 |
| JP | 2015-146871 A | 8/2015 |
| WO | WO 02/092312 A1 | 11/2002 |
| WO | WO 2012/017758 A1 | 2/2012 |
| WO | WO 2015/118958 A1 | 8/2015 |

* cited by examiner

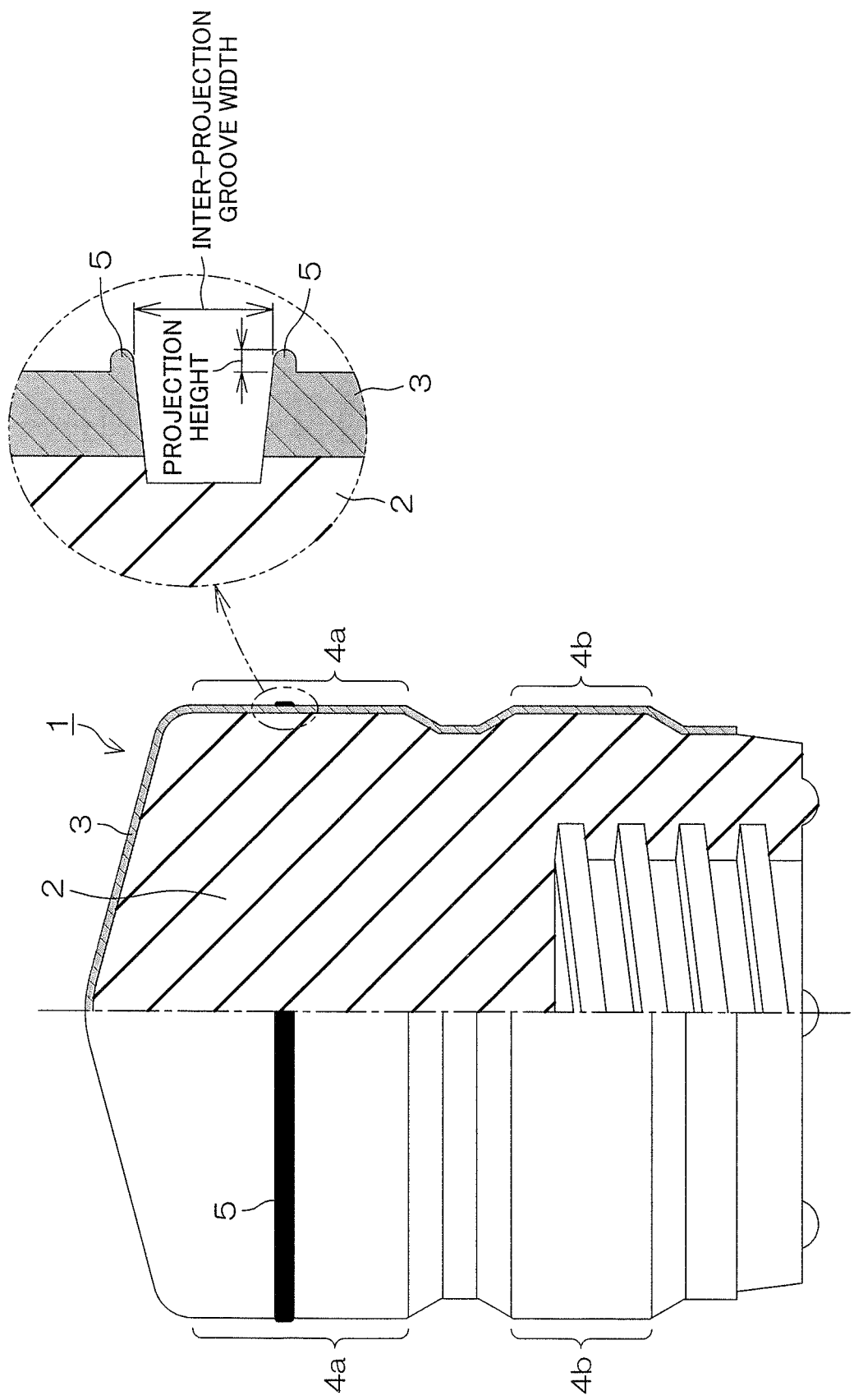

METHOD FOR PRODUCING SYRINGE GASKET, AND SYRINGE INCLUDING THE GASKET

TECHNICAL FIELD

The present invention relates to a method for producing a syringe gasket, and a medical syringe including the syringe gasket.

BACKGROUND ART

Syringes prefilled with a liquid drug (generally referred to as "prefilled syringes") are used as medical syringes. The prefilled syringes are advantageous because of their handling ease without the need for transferring the liquid drug into the syringes. Further, transfer of a wrong liquid drug into the syringe is advantageously prevented. Therefore, the prefilled syringes are increasingly used in recent years.

Unlike conventional syringes into which a liquid drug sucked up from a vial or other container is transferred immediately before use, the prefilled syringes are each required to serve as a container which is kept in contact with the liquid drug for a long period of time.

Such a syringe typically includes a syringe barrel, and a gasket fitted in the syringe barrel and slidable in the syringe barrel.

The gasket to be used for the syringe is generally made of a crosslinked rubber. It is known that the crosslinked rubber contains various crosslinking components, and these components and their thermally decomposed products are liable to migrate into the liquid drug when the liquid drug is kept in contact with the gasket. It is also known that these migrating components adversely influence the efficacy and the stability of some liquid drug.

Further, the gasket is required to be smoothly slidable in the syringe barrel when the syringe is used. In general, the gasket made of the crosslinked rubber is poorer in slidability. To cope with this, it is a general practice to apply silicone oil to an inner surface of the syringe barrel. However, it is also known that the silicone oil adversely influences the efficacy and the stability of some liquid drug.

In view of the foregoing, a product of so-called "laminated gasket" including a rubber gasket body and a highly slidable film laminated on a surface of the gasket body is often used for the medical syringe. Since the surface of the rubber gasket body of the laminated gasket is covered with the highly slidable film, it is possible to ensure the slidability even without the use of the silicone oil while preventing the components of the crosslinked rubber from migrating into the liquid drug (see Patent Documents 1 to 3).

In the laminated gasket, however, the film laminated on the surface is not elastic and, therefore, is liable to impair the elasticity of the inside crosslinked rubber. The elasticity of the gasket is an essential requirement for reliable sealing of the liquid drug contained in the syringe barrel. If the gasket has insufficient elasticity, the liquid drug contained in the syringe barrel is liable to leak out of the syringe barrel. Further, the slidability of the gasket inserted in the syringe barrel also requires improvement.

To cope with this problem, Patent Document 1 proposes a gasket laminated with a tetrafluoroethylene resin (PTFE) film by a casting method. However, this production method is a unique and impractical production method, and is liable to reduce the liquid sealability of the gasket because minute irregularities on a mold surface are transferred onto the surface of the lamination film.

Patent Document 2 proposes a laminated gasket which has a plurality of ring projections provided on a sliding surface thereof and having different outer shapes. However, the ring projections are problematic in slidability because of their greater widths.

Patent Document 3 proposes a production method for producing a laminated gasket which includes an inert resin film provided on a gasket body thereof as extending to a middle of a first annular seal portion thereof to be brought into contact with an inner wall of the syringe barrel. This production method allows for production of a smaller size gasket. However, it is difficult to produce a greater size gasket because of difficulty in stamping.

CITATION LIST

Patent Document

Patent Document 1: JP-HEI10(1998)-314305A
Patent Document 2: JP-2006-181027A
Patent Document 3: JP-2004-525011A
Patent Document 4: JP-2015-146871A

SUMMARY OF THE INVENTION

Problem to be Solved by the Invention

In a rubber product production process, rubber is generally vulcanization-molded in a mold having a cavity defining a desired product shape and, after the rubber is shaped, the resulting product is demolded from the mold. When the laminated gasket is produced by the conventional production process and a product of the laminated gasket is demolded from the mold, the product is rubbed against the mold and, therefore, minute scratches are formed on the surface of the laminated gasket. These minute scratches are liable to prevent the reliable sealing of the liquid drug (see, for example, Patent Document 4).

In view of the foregoing, it is a principal object of the present invention to provide a method for producing a syringe gasket which is improved in liquid drug sealability by forming a minute projection on a circumferential surface of the gasket after demolding the gasket.

Solution to Problems

To achieve the object, the present invention has the following features.

According to a first inventive aspect, there is provided a syringe gasket production method for producing a syringe gasket including a cylindrical main body made of an elastic material and an inert resin film laminated on a surface of the main body, the method including the step of: forming at least one minute projection extending circumferentially of the gasket on a surface of the inert resin film laminated on the main body by thermal processing using a laser beam.

According to a second inventive aspect, the inert resin film is highly heat-absorptive with respect to the wavelength of the laser beam in the syringe gasket production method.

According to a third inventive aspect, the inert resin film is black or brown in the syringe gasket production method.

According to a fourth inventive aspect, an inner surface of the inert resin film to be brought into contact with the surface of the main body is subjected to a surface texture modifying process before the inert resin film is laminated on the surface of the main body in the syringe gasket production method.

According to a fifth inventive aspect, the cylindrical main body has at least two circumferential surface portions located on a distal side and a proximal side thereof, and the minute annular projection is formed on a surface portion of the inert resin film present on a distal one of the circumferential surface portions in the syringe gasket production method.

According to a sixth inventive aspect, there is provided a medical syringe which includes a syringe gasket produced by the aforementioned production method, and a syringe barrel in which the syringe gasket is fitted.

Effects of the Invention

According to the present invention, the syringe gasket can be produced as having excellent sealability.

BRIEF DESCRIPTION OF THE DRAWING

FIGURE is a side elevation showing the construction of a syringe gasket according to an embodiment of the present invention with a half of the gasket illustrated in section.

EMBODIMENTS OF THE INVENTION

FIGURE is a side elevation showing the construction of a syringe gasket 1 according to an embodiment of the present invention with a half of the gasket illustrated in section.

The syringe gasket 1 includes a main body 2 made of an elastic material, and an inert resin film 3 laminated on a surface of the main body 2.

The main body 2 is simply required to be made of the elastic material, and the material for the main body 2 is not particularly limited. For example, the main body 2 may be made of any type of synthetic rubbers and thermoplastic elastomers, or a blend of any of these synthetic rubbers and thermoplastic elastomers. Particularly, a thermosetting rubber and a dynamically crosslinkable thermoplastic elastomer having crosslinking sites are preferred because of their excellent heat resistance. A polymer component to be employed for the material is not particularly limited, but usable examples of the polymer component include butyl rubber, halogenated butyl rubber, styrene butadiene rubber, butadiene rubber, epichlorohydrin rubber, neoprene rubber and ethylene propylene rubber.

The inert resin film 3 to be laminated on the surface of the main body 2 is simply required to be excellent in followability to the rubber. Usable examples of the inert resin film 3 include a polytetrafluoroethylene (PTFE) film, a modified polytetrafluoroethylene (modified PTFE) film, an ethylene-tetrafluoroethylene copolymer (ETFE) film and an ultrahigh molecular weight polyethylene (UHMWPE) film.

The expression "excellent in followability to the rubber" means that the inert resin film 3 has a tensile strength (breaking elongation) $E_B$ of, for example, not less than 300% and an adhesive force of not less than 1.2 N with respect to the rubber.

The inert resin film 3 is desirably a colored film. The color of the film is preferably a dark color such as black or brown, which is highly light-absorptive.

Where the inert resin film 3 is colored to be highly light-absorptive, minute projections can be advantageously formed on the film by thermal processing using a laser beam. That is, the minute projections can be formed as having a uniform inter-projection groove width and a uniform height.

Where the inert resin film 3 laminated on the surface of the main body 2 has the structure and the color described above, the minute projection can be advantageously formed on the circumferential surface of the inert resin film 3 laminated on the surface of the main body 2 by the thermal processing using the laser beam.

Referring to FIGURE, the laminated gasket 1 has circumferential surface portions 4a and 4b to be kept in gas-tight and liquid-tight contact with an inner surface of a syringe barrel. Annular minute projections 5 are provided on a distal circumferential surface portion 4a of the gasket 1 as extending circumferentially of the gasket 1.

In this embodiment, two annular projections 5 are provided on the circumferential surface portion 4a as extending circumferentially of the gasket by way of example.

It is merely necessary to provide at least one projection 5, but a plurality of projections may be provided to be spaced a predetermined distance from each other axially of the gasket 1. Thus, the number of the projections 5 is not particularly limited.

With the circumferential surface portion 4a of the gasket 1 being seen in development elevation, the projections 5 preferably extend generally linearly without local directionality.

When the gasket 1 is inserted into the syringe barrel, the projections 5 provided on the circumferential surface portion 4a of the gasket 1 are brought into press contact with the inner surface of the syringe barrel to locally increase a contact pressure between the gasket 1 and the syringe barrel, thereby improving the sealability. Further, increase in sliding resistance can be suppressed by the local increase in contact pressure.

The projections 5 may be formed after the gasket 1 is molded.

An exemplary method for the formation of the projections 5 is to apply heat to a surface layer of the laminated gasket 1 as a base to evaporate or decompose a surface portion of the inert resin film 3 and redeposit a part of the evaporated material to form the projections 5.

An exemplary method for applying the heat is to apply a laser beam. The processing by the application of the laser beam is preferred because it can form a minute projection structure and is less liable to influence the periphery of the projection formation area.

A known technique may be used for determination of the type and the output of the laser beam for the processing by the application of the laser beam. The type of the laser beam may be properly selected according to the material for the film, the height of the projections 5 and the like. A processing method using an infrared laser beam is preferred for industrial handling ease. A laser beam application period may be properly selected according to conditions for the formation of the projections. Particularly, application of a short-pulse laser beam is preferred because the periphery of the projection formation area is less liable to be thermally influenced.

Next, a method for producing the gasket 1 according to this embodiment will be described.

The gasket 1 according to this embodiment is produced through the following production process steps:

(1) preparing a gasket molding mold;
(2) molding a gasket laminated with an inert resin film 3 in the mold; and
(3) removing the laminated gasket from the mold, and then forming an annular projection extending circumferentially of the gasket on a circumferential surface portion of the gasket.

In the step of molding the gasket laminated with the inert resin film 3 in the mold, an unvulcanized rubber is put on the inert resin film 3 in the mold, and vulcanization-molded.

For example, the inert resin film is stacked on a sheet of an unvulcanized rubber containing a crosslinking agent, and the resulting stack is subjected to vulcanization-molding in the mold. Thus, the gasket is produced as having a predetermined shape.

In this case, an inner surface of the inert resin film 3 on which the rubber is to be stacked is preferably preliminarily roughened. With the inner surface of the inert resin film 3 roughened, the rubber can firmly adhere to the inert resin film 3 by the vulcanization molding without the use of an adhesive agent or the like. The adhesion is attributable to an anchoring effect which is created with the vulcanized rubber intruding into voids formed in the roughened inner surface of the inert resin film 3.

The modification of the inner surface of the inert resin film 3 may be achieved, for example, by applying an ion beam to the inner surface to break the internal molecular structure in the inner surface for the roughening (see, for example, JP4908617B).

The gasket can be produced as having more excellent sealability by molding the gasket in the mold, then demolding the gasket from the mold, and forming the projections 5 on the circumferential surface of the demolded gasket.

The formation of the projections after the molding of the gasket is achieved by the application of the laser beam as previously described.

EXAMPLES

Production of Gasket

A surface of an inert resin film was subjected to a roughening process, and the inert resin film was stacked on an unvulcanized rubber sheet of chlorinated butyl rubber (having a JIS A hardness of 58 degrees) with the roughened surface thereof in contact with the unvulcanized rubber sheet in a mold. Then, the resulting stack was subjected to vulcanization molding at 175° C. for 6 minutes by a vacuum press, thereby producing a gasket structure with the rubber vulcanization-bonded to the surface of the inert resin sheet.

The following inert resin films were used in respective examples.
(1) A 100-μm thick black polytetrafluoroethylene (PTFE) film available from Guaniflon Inc. was used in Example 1.
(2) A 40-μm thick brown polytetrafluoroethylene (PTFE) film available from Chukoh Chemical Industries, Ltd. was used in Example 2.
(3) A 100-μm thick black polytetrafluoroethylene (PTFE) film available from Guaniflon Inc. was used in Comparative Example 1.
(4) A 100-μm thick translucent skived PTFE film available under the trade name of VALFLON from Nippon Valqua Industries, Ltd. was used in Comparative Example 2.

Gasket products of Examples 1 and 2 were each produced by demolding the gasket structure produced in the aforementioned manner and then forming annular projections extending circumferentially on a circumferential surface portion of the gasket structure. Gasket products of Comparative Examples 1 and 2 were each produced by demolding the gasket structure produced in the aforementioned manner without forming the annular projections.

[Formation of Projections]

The formation of the projections was achieved through the laser beam processing by applying a laser beam at a wavelength of 9300 nm by means of 3-Axis CO2 Laser Marker ML-Z9550T available from Keyence Corporation.

[Test Method]

Observation of Projections

The gasket products thus produced were each attached and fixed to a plunger, and the height of the projections and the inter-projection groove width were measured at four positions on each of the products by a laser microscope (available from Keyence Corporation). Averages of the measurements are shown in Table 1.

Liquid Drug Sealability

A test sample was produced by inserting each of the gasket products into a syringe barrel made of a cycloolefin resin and having an inner diameter ϕ of 6.35 mm. The test sample was filled with a test liquid, and then an opposite end of the syringe barrel was capped. The test sample was allowed to stand still at 40° C. for 2 months, and then observed with an objective lens having a magnification of 50× by means of a video microscope (DVM5000 available from Leica Microsystems Inc.) to be checked for liquid leakage. For each test sample, 10 products were observed, and the number of products suffering from liquid leakage (in which the test liquid penetrated beyond a maximum diameter portion of the gasket) was recorded. A test sample with two or less products suffering from the liquid leakage was rated as acceptable. The test liquid herein used was prepared by adding 0.2 g/L of a colorant (red food colorant available from Tokyo Chemical Industry Co., Ltd.) and 1.0 g/L of a surfactant (POLYSORBATE 80 available from NOF Corporation) to water.

[Test Results]

TABLE 1

|  | Example 1 | Example 2 | Comparative Example 1 | Comparative Example 2 |
|---|---|---|---|---|
| Type of film | Black | Brown | Black | Translucent |
| Thermal processing | Done | Done | Undone | Undone |
| Projections | | | | |
| Projection height (μm) | 19 to 24 | 20 to 25 | — | — |
| Groove width (μm) | 135 to 175 | 140 to 180 | — | — |
| Liquid drug sealability | 0/10 | 0/10 | 8/10 | 6/10 |

As shown in Table 1, it was confirmed that the laminated gaskets of Examples 1 and 2 produced as having the minute annular projections by using a color film having higher followability to the rubber were excellent in liquid drug sealability.

This application corresponds to Japanese Patent Application No. 2017-110359 filed in the Japan Patent Office on Jun. 2, 2017, the disclosure of which is incorporated herein by reference in its entirety.

What is claimed is:

1. A syringe gasket production method comprising the steps of:
preparing a syringe gasket including a cylindrical main body made of an elastic material and an inert resin film laminated on a surface of the main body; and
forming at least one minute projection extending circumferentially of the gasket on a surface of the inert resin film laminated on the main body by thermal processing using a laser beam,
wherein an inner surface of the inert resin film to be brought into contact with the surface of the main body is subjected to a surface texture modifying process before the inert resin film is laminated on the surface of the main body.

2. The syringe gasket production method according to claim 1, wherein the inert resin film is highly heat-absorptive with respect to a wavelength of the laser beam.

3. The syringe gasket production method according to claim 2, wherein the inert resin film is black or brown.

4. The syringe gasket production method according to claim 1,
wherein the cylindrical main body has at least two circumferential surface portions located on a distal side and a proximal side thereof,
wherein the minute annular projection is formed on a surface portion of the inert resin film present on a distal one of the circumferential surface portions.

5. A medical syringe comprising:
a syringe gasket produced by the production method according to claim 1; and
a syringe barrel in which the syringe gasket is fitted.

6. A syringe gasket production method comprising the steps of:
preparing a syringe gasket including a cylindrical main body made of an elastic material and an inert resin film laminated on a surface of the main body; and
forming at least one groove extending circumferentially of the gasket on a surface of the inert resin film laminated on the main body by thermal processing using a laser beam,
wherein the groove has a width of 135 μm to 180 μm and has minute projections at both edges of the groove which are formed by redepositing a part of evaporated materials while the groove is formed using a laser beam.

7. The syringe gasket production method according to claim 6, wherein the inert resin film is highly heat-absorptive with respect to a wavelength of the laser beam.

8. The syringe gasket production method according to claim 7, wherein the inert resin film is black or brown.

9. The syringe gasket production method according to claim 6, wherein an inner surface of the inert resin film to be brought into contact with the surface of the main body is subjected to a surface texture modifying process before the inert resin film is laminated on the surface of the main body.

10. The syringe gasket production method according to claim 6,
wherein the cylindrical main body has at least two circumferential surface portions located on a distal side and a proximal side thereof,
wherein the groove is formed on a surface portion of the inert resin film present on a distal one of the circumferential surface portions.

11. A medical syringe comprising:
a syringe gasket produced by the production method according to claim 6; and
a syringe barrel in which the syringe gasket is fitted.

* * * * *